(12) United States Patent
Lamoncha (10) Patent No.: US 11,865,261 B2
(45) Date of Patent: Jan. 9, 2024

(54) RESPIRATOR MASK

(71) Applicant: Mark Lamoncha, Columbiana, OH (US)

(72) Inventor: Mark Lamoncha, Columbiana, OH (US)

( * ) Notice: Subject to any disclaimer, the term of this patent is extended or adjusted under 35 U.S.C. 154(b) by 587 days.

(21) Appl. No.: 17/038,833

(22) Filed: Sep. 30, 2020

(65) Prior Publication Data

US 2022/0016376 A1 Jan. 20, 2022

Related U.S. Application Data

(60) Provisional application No. 63/051,490, filed on Jul. 14, 2020.

(51) Int. Cl.
*A61M 16/06* (2006.01)

(52) U.S. Cl.
CPC .... *A61M 16/0672* (2014.02); *A61M 16/0605* (2014.02); *A61M 16/0683* (2013.01); *A61M 2209/088* (2013.01)

(58) Field of Classification Search
CPC ....... A61M 15/08; A61M 15/085; A62B 7/02; A62B 9/06; A62B 18/02; A62B 18/025; A62B 18/08; A62B 18/082; A62B 23/02; A62B 23/06
See application file for complete search history.

(56) References Cited

U.S. PATENT DOCUMENTS

| | | | |
|---|---|---|---|
| 2,388,626 A | 11/1945 | Wilson | |
| 2,393,955 A | 2/1946 | Baratelli et al. | |
| 2,574,749 A | 11/1951 | Mendelsohn | |
| 3,298,031 A | 1/1967 | Morgan | |
| 3,531,188 A | 9/1970 | LeBlanc et al. | |
| 3,991,753 A | 11/1976 | Viesca y Viesca | |
| 4,231,364 A | 11/1980 | Speshyock | |
| 4,280,491 A | 7/1981 | Berg et al. | |
| 4,764,167 A | 8/1988 | Tu | |
| 4,790,306 A | 12/1988 | Braun et al. | |
| 4,796,621 A | 1/1989 | Barle et al. | |
| 4,821,340 A | 4/1989 | Johnson | |
| 4,832,018 A | 5/1989 | Pantaleon-Stemberg | |
| 4,850,346 A | 7/1989 | Michel et al. | |

(Continued)

OTHER PUBLICATIONS

ChicMe, Face Mask with Clear Window Visible Expression for the Deaf and Hard of Hearing, site visited Aug. 19, 2020, https://www.chicme.com/product/face_mask_with_clear_window_visible_expression_for_the_deaf_and_hard_of_hearing/7a76007a-3d75-4f4f-b443-f2a8cb6d0db0.html.

(Continued)

*Primary Examiner* — Valerie L Woodward
(74) *Attorney, Agent, or Firm* — Standley Law Group LLP; Jeffrey S. Standley; Adam J. Smith (57) ABSTRACT

A respirator mask that includes a body, a nasal interface, and a mouthpiece. The body defines an exterior surface and an interior space. The mouthpiece includes an inner channel that is insertable into a human mouth, wherein the inner channel extends outward from the exterior surface of the body and defines an opening into the interior space. The nasal interface includes a recessed portion that is recessed into the body and is configured to receive at least part of a human nose. The nasal interface further includes a pair of nozzles, wherein each nozzle of the pair of nozzles is insertable into a nostril of a wearer and defines an opening into the interior space.

14 Claims, 6 Drawing Sheets

(56) References Cited

U.S. PATENT DOCUMENTS

| | | | |
|---|---|---|---|
| 4,924,526 A | 5/1990 | Parissenti et al. | |
| 4,934,361 A | 6/1990 | Michel et al. | |
| 4,965,887 A | 10/1990 | Paoluccio et al. | |
| 5,062,421 A | 11/1991 | Burns et al. | |
| 5,086,768 A | 2/1992 | Niemeyer | |
| 5,181,507 A | 1/1993 | Michel et al. | |
| 5,240,478 A | 8/1993 | Messina | |
| 5,265,595 A * | 11/1993 | Rudolph | A61M 16/0616 128/204.23 |
| H1316 H | 6/1994 | McGuinness | |
| 5,331,957 A | 7/1994 | Liu | |
| 5,392,773 A | 2/1995 | Bertrand | |
| 5,416,923 A | 5/1995 | Peugh | |
| 5,463,693 A | 10/1995 | Birli et al. | |
| 5,471,679 A | 12/1995 | Paoluccio | |
| 5,505,197 A | 4/1996 | Scholey | |
| 5,765,223 A | 6/1998 | McCausland | |
| 5,957,131 A | 9/1999 | Hutchinson et al. | |
| 5,996,580 A | 12/1999 | Swann | |
| 6,298,849 B1 | 10/2001 | Scholey et al. | |
| 6,408,845 B1 | 6/2002 | Pereira et al. | |
| 6,497,232 B2 | 12/2002 | Fecteau et al. | |
| 6,497,756 B1 | 12/2002 | Curado et al. | |
| 6,536,435 B1 | 3/2003 | Fecteau et al. | |
| 6,543,450 B1 | 4/2003 | Flynn | |
| 6,584,975 B1 * | 7/2003 | Taylor | A62B 23/06 128/206.13 |
| 6,604,524 B1 | 8/2003 | Curran et al. | |
| 6,684,882 B1 | 2/2004 | Morine | |
| 6,758,212 B2 * | 7/2004 | Swann | A62B 17/04 128/206.29 |
| 6,763,835 B1 | 7/2004 | Grove et al. | |
| 6,957,653 B2 | 10/2005 | Campbell et al. | |
| 6,959,709 B2 | 11/2005 | Curran et al. | |
| 7,007,695 B2 | 3/2006 | Curran et al. | |
| 7,082,944 B2 | 8/2006 | Gossweiler | |
| 7,188,623 B2 | 3/2007 | Anderson et al. | |
| 7,294,175 B2 | 11/2007 | Huang et al. | |
| 7,594,278 B2 | 9/2009 | Huh | |
| 7,878,202 B2 | 2/2011 | Anderson et al. | |
| 8,192,523 B1 | 6/2012 | Kaufman et al. | |
| 8,211,226 B2 | 7/2012 | Bredt et al. | |
| 9,084,416 B2 | 7/2015 | Steen et al. | |
| 9,192,793 B2 | 11/2015 | Patil et al. | |
| 9,192,796 B2 | 11/2015 | Patil et al. | |
| 9,408,424 B2 | 8/2016 | Noh et al. | |
| 9,468,782 B2 | 10/2016 | Koehler | |
| 9,596,842 B2 | 3/2017 | Steen et al. | |
| 10,207,129 B2 | 2/2019 | Koehler | |
| 10,213,629 B2 | 2/2019 | Tobias | |
| 10,556,136 B2 | 2/2020 | Seppala et al. | |
| 2002/0078953 A1 | 6/2002 | Fecteau et al. | |
| 2004/0007234 A1 | 1/2004 | Duxbury | |
| 2004/0025878 A1 | 2/2004 | Duxbury | |
| 2004/0237962 A1 * | 12/2004 | Russell | G02C 11/00 128/201.15 |
| 2005/0051169 A1 | 3/2005 | Gossweiler | |
| 2005/0150385 A1 | 7/2005 | Huang et al. | |
| 2006/0005841 A1 | 1/2006 | Anderson et al. | |
| 2006/0081249 A1 | 4/2006 | Duxbury | |
| 2006/0201513 A1 | 9/2006 | Chu | |
| 2006/0207605 A1 | 9/2006 | Anderson et al. | |
| 2007/0240719 A1 | 10/2007 | Duarte | |
| 2008/0223370 A1 * | 9/2008 | Kim | A41D 13/11 128/206.17 |
| 2010/0065058 A1 | 3/2010 | Ungar et al. | |
| 2012/0184024 A1 | 7/2012 | Steen et al. | |
| 2014/0116430 A1 | 5/2014 | Patil et al. | |
| 2014/0283842 A1 * | 9/2014 | Bearne | A61M 16/0616 128/206.24 |
| 2015/0020800 A1 | 1/2015 | Tobias | |
| 2015/0053206 A1 | 2/2015 | Seppala et al. | |
| 2015/0342178 A1 | 12/2015 | Steen et al. | |
| 2016/0001101 A1 | 1/2016 | Sabolis et al. | |
| 2016/0213959 A1 | 7/2016 | Barklow | |
| 2016/0332008 A1 | 11/2016 | McAndrews | |
| 2017/0273626 A1 | 9/2017 | MacDonald | |
| 2017/0361531 A1 | 12/2017 | Hasskerl et al. | |
| 2019/0126542 A1 | 5/2019 | Poppe et al. | |
| 2019/0127598 A1 | 5/2019 | Bernhardt et al. | |
| 2019/0255370 A1 | 8/2019 | Seppala et al. | |
| 2019/0299520 A1 | 10/2019 | Wieber et al. | |
| 2019/0321663 A1 | 10/2019 | Nestelroad et al. | |
| 2020/0108218 A1 | 4/2020 | Bock-Aronson et al. | |
| 2021/0275842 A1 * | 9/2021 | Conrad | A62B 18/025 |
| 2021/0319777 A1 * | 10/2021 | Wang | H04R 1/08 |

OTHER PUBLICATIONS

ClearMask, The ClearMask, site visited Aug. 19, 2020, https://www.theclearmask.com/product.

Etsy, site visited Aug. 19, 2020, https://www.etsy.com/market/clear_mask.

FilterSpec, Filterspec PRO Goggle FFP3V Valved, site visited Aug. 19, 2020, https://www.jspsafety.com/link/en/respiratory-protection/filterspec-integrated-protection/filterspec-pro/filterspec-pro-goggle-ffp3v-valved/age130-201-100/p/?parm=CAT1JSP&prdcod=AGE130-201-100.

Good Housekeeping, Where to Buy Clear Face Masks with Windows for Lip Reading, site visited Aug. 19, 2020, https://www.goodhousekeeping.com/health/g33471599/best-clear-face-masks/.

Jackson Safety, Jackson Safety 18629 V90 Goggle and Faceshield, Standard, Clear with Blue Tint, site visited Aug. 19, 2020, https://www.amazon.com/Jackson-Safety-18629-Faceshield-Standard/dp/B00KTEM046.

Unique Gadgets & Toys, Safety Face Shield Reusable Goggle Shield Wearing Glasses Face Visor Transparent Anti-Fog Layer Protect Eyes from Splash, site visited Aug. 19, 2020, https://www.amazon.com/Reusable-Wearing-Glasses-Transparent-Anti-Fog/dp/B087F2CNKH/ref=sr_1_6?dchild=1&keywords=Unique+Gadgets+%26+Toys&qid=1603913032&sr=8-6.

Additive Manufacturing, 3D Printing and Coronavirus: U.S. Additive Manufacturers Share Their Experiences, May 19, 2020, https://www.additivemanufacturing.media/blog/post/3d-printing-and-coronavirus-us-additive-manufacturers-share-their-experiences.

\* cited by examiner

RESPIRATOR MASK

CROSS-REFERENCE TO RELATED APPLICATION

This application is a non-provisional patent application and makes a priority claim to U.S. Provisional Application No. 63/051,490, filed Jul. 14, 2020.

TECHNICAL FIELD

Exemplary embodiments of the present invention relate generally to a respirator face mask.

BACKGROUND

Respirators are designed to protect a wearer from inhaling harmful gasses and/or particulate matter such as dusts, fumes, airborne microorganisms, viruses, and the like. Typically, the wearer selects a suitable type of respirator based on the environment in which he/she will be wearing it. For example, passive air-purifying respirators that only cover a portion of the wearer's face may be suitable for cities and public places to protect against air pollution and infectious diseases. On the other hand, full-face supplied-air respirators, which offer a much higher degree of protection, may be worn at worksites or other hazardous places where the level of airborne particular matter is relatively high (e.g., construction zones and/or by firefighters). The suitability of any particular type of respirator for any particular application depends largely, if not entirely, on its design.

Outbreaks of viral respiratory illness, such as the 2002-2004 SARS outbreak and the 2019-2020 Coronavirus pandemic, have caused widespread shortages of personal protective equipment. In particular, respirators have rapidly come into short supply, prompting those in desperate need of respirators to rely on respirators that may be less than suitable by design. Some have even opted to fashion their own respirators out of household materials. Accordingly, a respirator design that may be suitable for hospital applications is desired.

SUMMARY OF THE INVENTION

Disclosed are respirator masks that include a body, a nasal interface, and a mouthpiece.

In one embodiment of the present invention, the respirator mask includes a body that defines an exterior surface and an interior space. The mouthpiece includes an inner channel that is insertable into a human mouth, wherein the inner channel extends outward from the exterior surface of the body and defines an opening into the interior space. The nasal interface includes a recessed portion that is recessed into the body and is configured to receive at least part of a human nose. The nasal interface further includes a pair of nozzles, wherein each nozzle of the pair of nozzles is insertable into a nostril of a wearer and defines an opening into the interior space.

In another embodiment of the present invention, the respirator mask includes a body that defines an exterior surface, an interior space, and a first opening into the interior space, wherein the first opening is configured to intake external air. The mouth includes an inner channel that is insertable into a human mouth, wherein the inner channel extends outward from the exterior surface of the body and defines a second opening into the interior space. The mouthpiece further includes an outer ridge extending from the exterior surface of the body that is configured to surround and enclose at least part of the wearer's mouth. The nasal interface includes a recessed portion that is recessed into the body and is configured to receive at least part of a human nose. The nasal interface further includes a first nozzle and a second nozzle, wherein the first nozzle and the second nozzle are each insertable into a nostril of a wearer, and wherein the first nozzle defines a third opening into the interior space and the second nozzle defines a fourth opening into the interior space.

In yet another embodiment of the present invention, the respirator mask includes a body that defines an exterior surface and an interior space. The body also includes an attachment feature configured to attach the body to a pair of glasses. The mouthpiece includes an inner channel that is insertable into a human mouth, wherein the inner channel extends outward from the exterior surface of the body and defines an opening into the interior space. The nasal interface includes a recessed portion that is recessed into the body and is configured to receive at least part of a human nose. The nasal interface further includes a pair of nozzles, wherein each nozzle of the pair of nozzles is insertable into a nostril of a wearer and defines an opening into the interior space.

Other examples of the disclosed respirator mask will become apparent from the following detailed description, the accompanying drawings and the appended claims.

DETAILED DESCRIPTION

Figure 1:
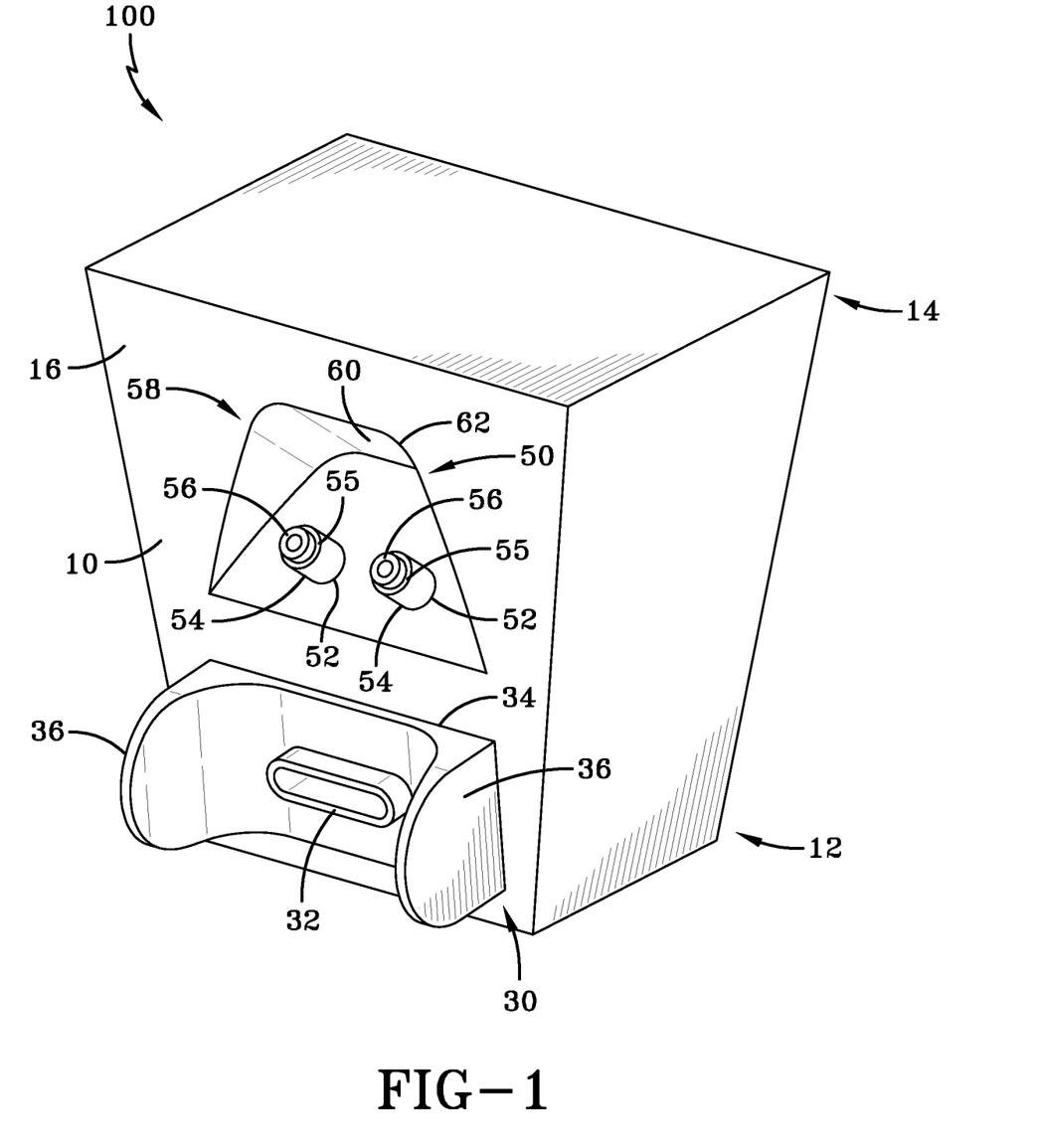
FIG. 1 is a perspective view of an embodiment of the respirator mask.

Referring to FIG. 1, the present disclosure provides examples of a respirator mask 100 that includes a body 10, a mouthpiece 30 and a nasal interface 50. The respirator mask 100 may be worn on the face of a wearer by positioning the mouthpiece 30 at least partially in the wearer's mouth and the nasal interface 50 in close proximity with the wearer's nose. Various embodiments of the respirator mask 100 may be sized and shaped as appropriate to closely fit the face of a wearer. Ideally, the respirator mask 100 may be configured such that a substantially airtight environment may be maintained between the respirator mask 100 and the wearer's nose and mouth.

The various components of the respirator mask 100 (e.g., the body 10, the mouthpiece 30, and the nasal interface 50) may be fabricated out of any suitable material. However, since the respirator mask 100 is designed to be worn on the wearer's face, it is generally contemplated that the various components should be fabricated out of a substantially rigid material (so as to withstand prolonged use) that is also water resistant (so as to avoid degradation). For example, materials such as glass, metal, and plastic may be suitable for such a purpose, and need not be the same for each individual component. Further, in a preferred example, plastics such as polystyrene and/or polyvinyl acetate may be used so that the various components, either individually or collectively, may be fabricated via additive manufacturing (3D printing). In another exemplary example, the entire respirator mask 100 may be additively manufactured as a single monolithic piece.

In the example shown, the body 10 is shaped as a trapezoidal prism having a narrow base 12 and a wider top 14 (e.g., cowbell shaped). Without being bound by any particular theory, it is generally contemplated that the downward taper of the body 10 helps to prevent the respirator mask 100 from slipping out of the wearer's hand while the wearer is holding the respirator mask 100 up to the wearer's face. Further, the body 10 defines a front surface 16 that includes the mouthpiece 30 and the nasal interface 50. As shown, the mouthpiece 30 and the nasal interface 50 may both be centered along the width of the front surface 16, with the nasal interface 50 being disposed along the top 14 of the body 10 and the mouthpiece 30 being disposed along the base 12. Various other examples of the respirator mask 100 (e.g., FIGS. 5 and 6) may vary from the example shown in terms of size, shape (e.g., curved, irregular, and other polygonal shapes), and configuration (e.g., locations of the mouthpiece 30 and nasal interface 50 along the front surface 16, and the relative spacing therebetween). However, those skilled in the art will appreciate that these variations will not result in a departure from the scope of the present disclosure.

Figure 2:
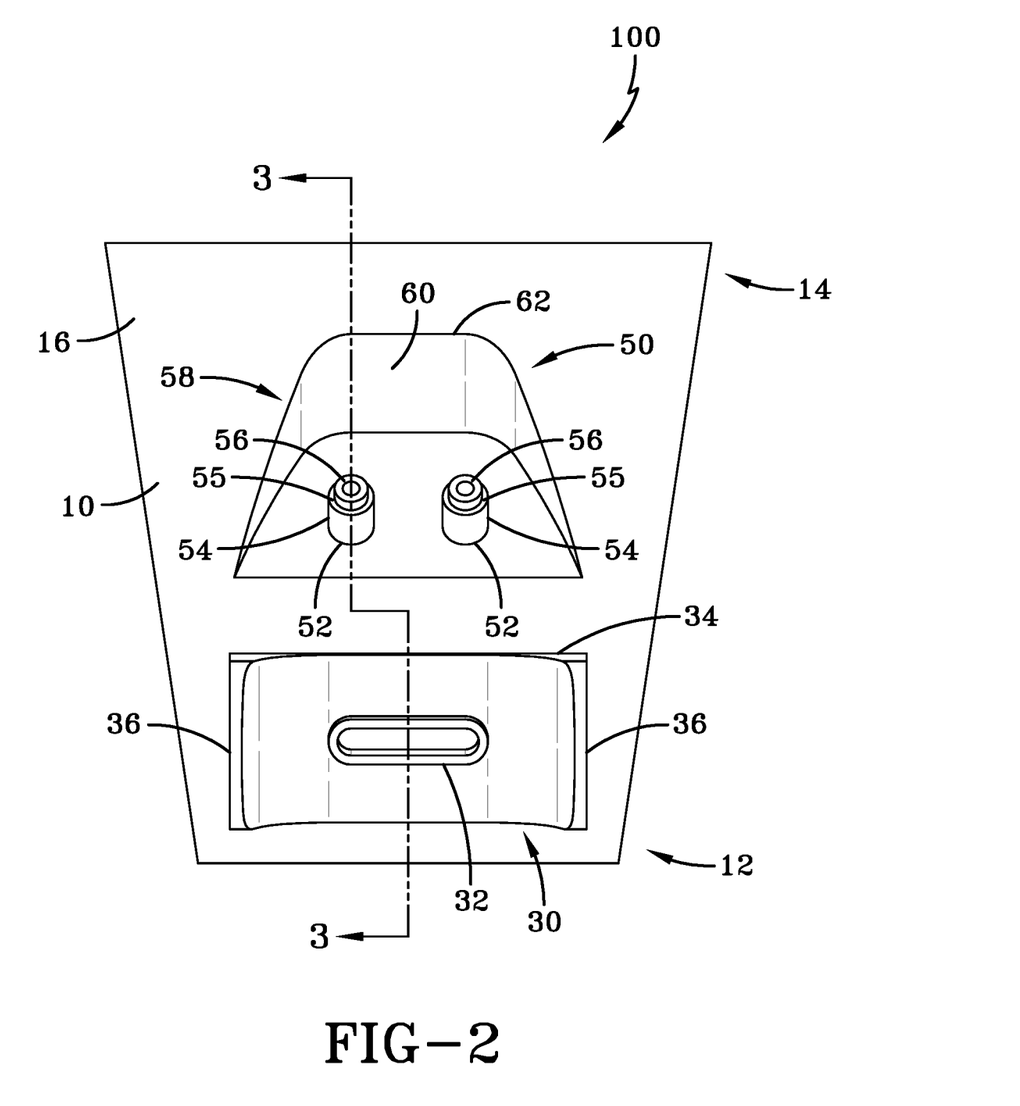
FIG. 2 is a front elevation view of the respirator mask of FIG. 1.
Figure 3:
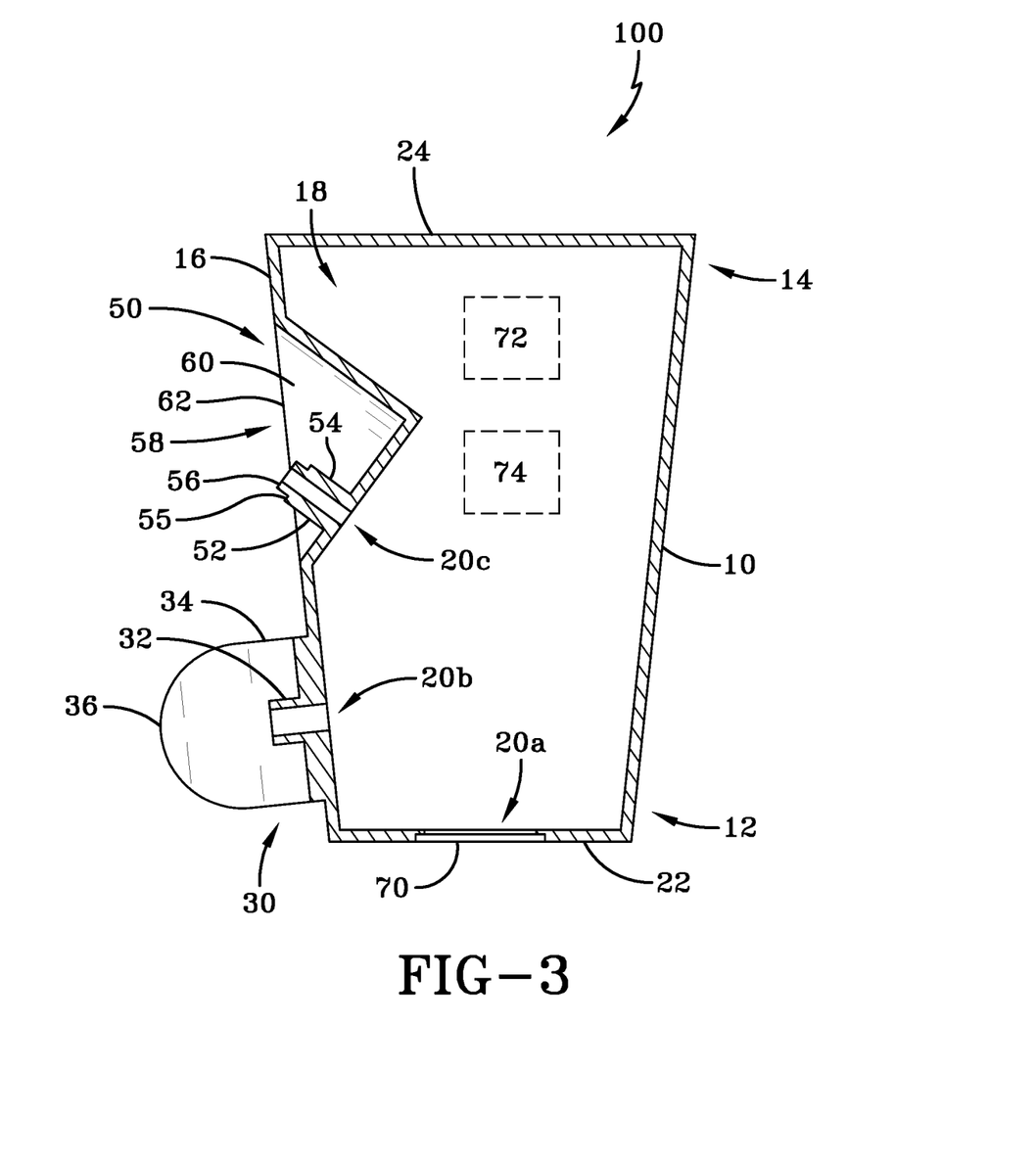
FIG. 3 is a side cross-sectional view of the respirator mask of FIG. 1.

Referring to FIGS. 2 and 3, the body 10 includes an interior space 18 and a number of openings 20 into the interior space 18. These openings 20 may enable the flow of air into the interior space 18, and either to or from the wearer. For example, the respirator mask 100 shown includes opening 20a disposed along the bottom side 22 of the body 10 (FIG. 4), another opening 20b leading into the mouthpiece 30, and two openings 20c leading into the nasal interface 50 (FIG. 3 shows one). The size, shape, and location of these openings 20a-20c need not be limiting features, and may also vary without departing from the scope of the present disclosure. The purpose of each of these openings 20a-20c is discussed in greater detail below.

Referring specifically to FIG. 3, the mouthpiece 30 includes an inner channel 32 and an outer ridge 34, both extending from the front surface 16 of the body 10. When the wearer puts on the respirator mask 100, the inner channel 32 may be at least partially inserted into the wearer's mouth while the outer ridge 34 surrounds the wearer's mouth to enclose it. In effect, the inner channel 32 provides a direct path for air to flow between the interior space 18 and the wearer's mouth, while the outer ridge 34 seals the external area surrounding the wearer's mouth such that the wearer only breathes air from the interior space 18.

As shown, the inner channel 32 functions as an extension of opening 20b and is partially defined by it. Further, both the inner channel 32 and opening 20b may be elongated along the width of the body 10 to increase the flow of air to and from the mouth. Those skilled in the art will appreciate, however, that this is just one non-limiting example and that other configurations are certainly possible. For example, configurations involving multiple inner channels 32, or multiple openings 20b leading into a single inner channel 32, may also be employed without departing from the scope of the present disclosure.

The outer ridge 34 is designed to wrap around, and thereby enclose (e.g., cover) the wearer's mouth. In the configuration shown, the outer ridge 34 may define a generally rectangular cross-section (parallel to the front surface 16, as best shown in FIG. 2) and may define an inward, longitudinal curve along the width of the body 10. Due to this curve, the outer ridge 34 may further define a pair of opposing, longitudinal ends 36 that extend the furthest outward relative to the front surface 16 of the body 10. This crescent shape enables the mouthpiece 30 to accommodate the curved shape of the human head such that even the corners of the mouth are covered.

The nasal interface 50 includes at least one nozzle 52, preferably two, extending from the front surface 16 of the body 10. Each nozzle 52 includes a proximal portion 54 and a distal portion 56, wherein the proximal portion 54 includes an end surface 55 that the distal portion 56 extends from. As shown, the proximal portion 54 and the distal portion 56 may be coaxial relative to one another, and may both be generally cylindrical in shape. In use, the distal portion 56 may be inserted into a wearer's nostril until the end surface 55 of the proximal portion 54 contacts the exterior surface of the nostril (e.g., the columella). By doing so, a seal may be created between said exterior surface and the end surface 55 of the proximal portion 54. In exemplary examples, the nozzle(s) 52 may also be angled upwards to correspond with the downward orientation of the nasal cavity.

In one or more examples, the nasal interface 50 may also include a recessed portion 58 defined in the body 10 of the respirator mask 100. This recessed portion 58 may be sized and shaped to receive the forward part of the wearer's nose (e.g., the apex and/or the dorsum nasi), thereby enabling closer engagement with the respirator mask 100. Further, the recessed portion 58 includes an inside surface 60 that defines an edge 62 with the front surface 16 of the body 10 (e.g., at the interface between them). Ideally, this edge 62 may be shaped as appropriate to correspond with the curvature of the human nose (e.g., across the nasal bridge). Thus, when the respirator mask 100 is worn by the wearer, the seal between the exterior surface of the nostril and the end surface 55 of the proximal portion 54, plus the close engagement between the edge 62 of the recessed portion 58 and the bridge of the wearer's nose, cumulatively ensures that only air from the interior space 18 enters the wearer's nose.

At this point, those skilled in the art will appreciate that the respirator mask 100 may be adapted for either passive air-purifying or active supplied-air respirator systems. For example, by coupling opening 20a to tubing/hosing, the respirator mask 100 may be fluidly connected to a contained air source, thereby enabling the contained air to flow into the interior space 18 before exiting the respirator mask 100 into the wearer's nose and/or mouth. The seals created between the respirator mask 100 and the wearer's nose and mouth ensure that the wearer only breathes the contained air, and that minimal, if any, contained air is lost. To be clear, "air" as used herein refers generally to any type of breathable gas, including those other than atmospheric air. As such, the contained air systems described above may include, for example, oxygen tanks and the like without departing from the scope of the present disclosure.

Figure 4:
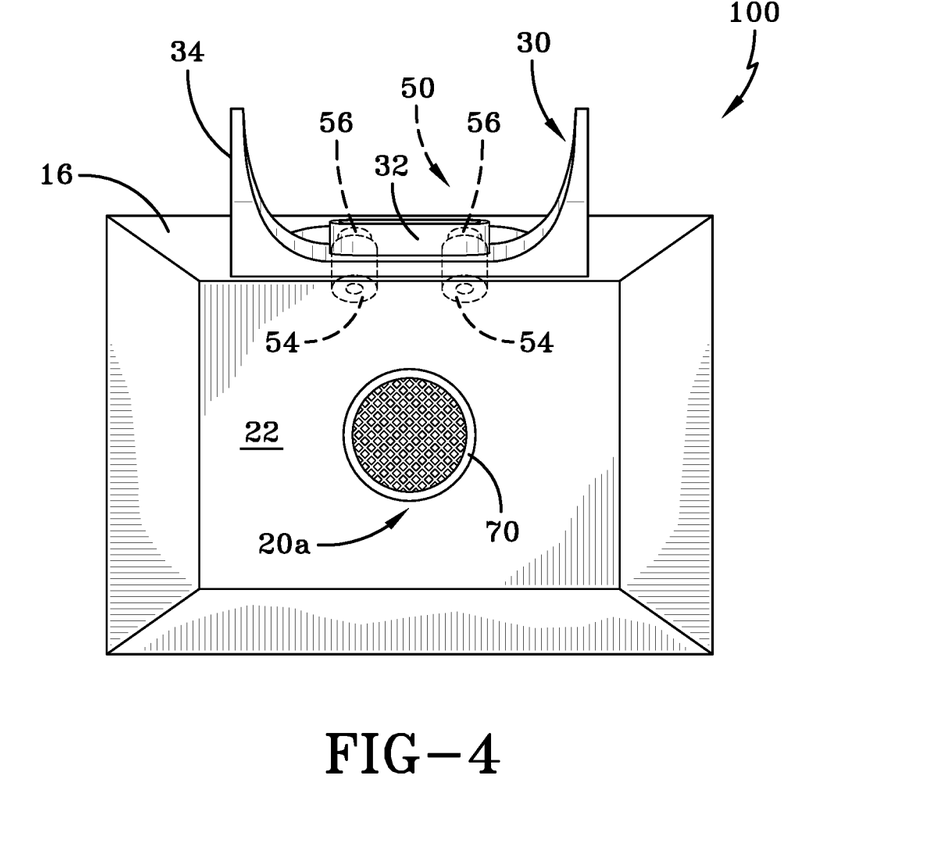
FIG. 4 is a bottom view of an alternative embodiment of the respirator mask.

Alternatively, the respirator mask 100 may be configured to intake, and then filter, external air instead of drawing air from a contained air source. Referring to FIG. 4, opening 20a would not be coupled to a tube/hose, but would instead be used to intake external air (e.g., external to the respirator mask 100). If needed, additional and/or larger openings may also be provided to increase external air intake (e.g., along the top side 24 of the body 10). Whatever the configuration, each opening 20a that does not lead into either the mouthpiece 30 or the nasal interface 50 may (but preferably should) be provided with a filtration member 70 to prevent unwanted contamination from entering the interior space 18 of the body 10. These filtration members 70 may include any suitable type of filter, such as, for example, passive air filters containing filtration material (e.g., spun fiberglass, pleated paper, cloth, activated carbon, etc.) that filter particulate matter based on particle size. Alternatively, or additionally, one or more active filtration methods may also be employed, such as, for example, ultraviolet germicidal irradiation, air ionizers, and the like.

As an additional feature, regardless of whether the respirator mask 100 is configured to be passive (air-purifying) or active (supplied-air), an interior filter 72 may further be provided within the interior space 18 of the body 10 (shown schematically in FIG. 3). Like with the filter members 70, the interior filter 72 may include any suitable type of filter, such as, but not limited to, those described above.

In one or more examples, the respirator mask 100 may also include a communication device 74 (shown schematically in FIG. 3) for facilitating communication by the wearer while the wearer is wearing the respirator mask 100. For example, a speech projector may be included so that the wearer may project (i.e., broadcast or amplify) his/her voice to the immediate surroundings. In another example, a microphone transmitter may be included to further transmit the wearer's voice to a suitable receiver. Whatever the case, it is generally contemplated that an optimum location for the communication device 74 would be proximate (e.g., at or near) the mouthpiece 30. As shown, the interior space 18 of the body 10 may be one example of such a location.

In a preferred embodiment, the wearer may put on the respirator mask 100 by inserting the nozzles 52 into the wearer's nostrils, inserting the inner channel 32 into wearer's mouth, and bringing the respirator mask 100 into close enough proximity with the wearer's face such that a seal is created around the wearer's mouth by the outer ridge 34 of the mouthpiece 30, and around the wearer's nostrils by proximal portions 54 of the nozzles 52. Further, an interior filter 72 and a communication device 74 may be provided within the interior space 18 of the body 10. The wearer, after putting on the respirator mask 100, may then breath through the openings 20b, 20c in the nozzles 52 and the inner channel 32, and communicate as needed by way of the communication device 74.

Figure 5:
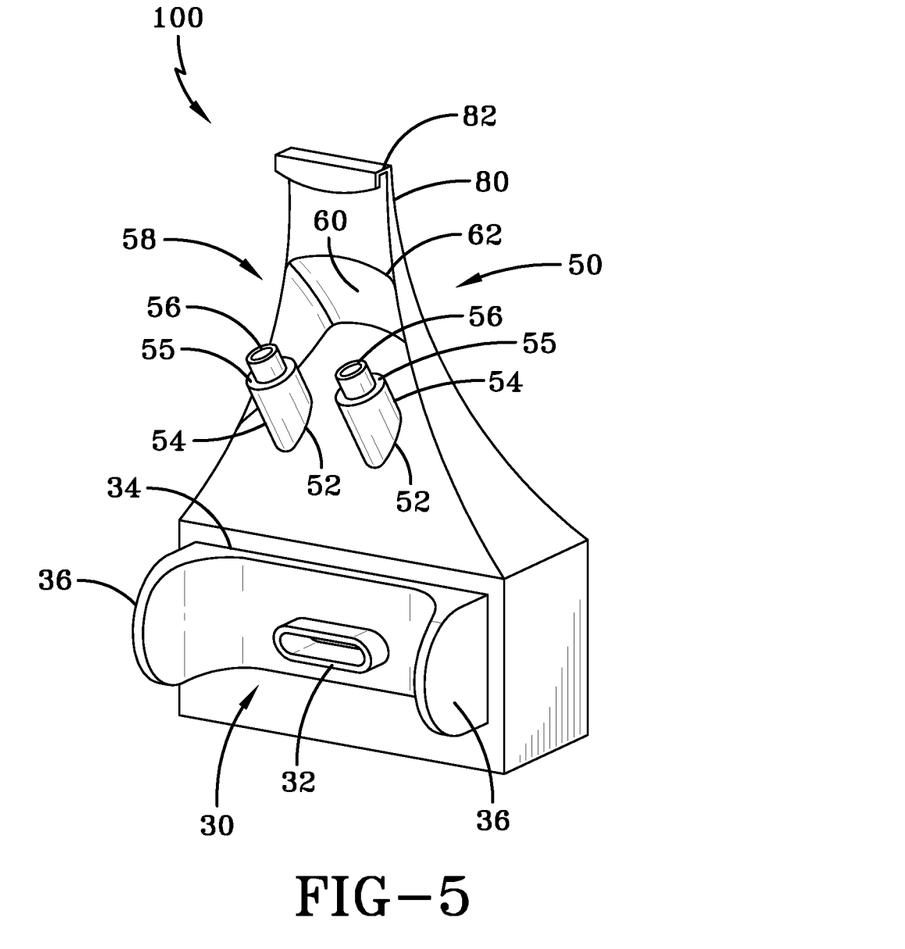
FIG. 5 is a perspective view of a second embodiment of the respirator mask.
Figure 6:
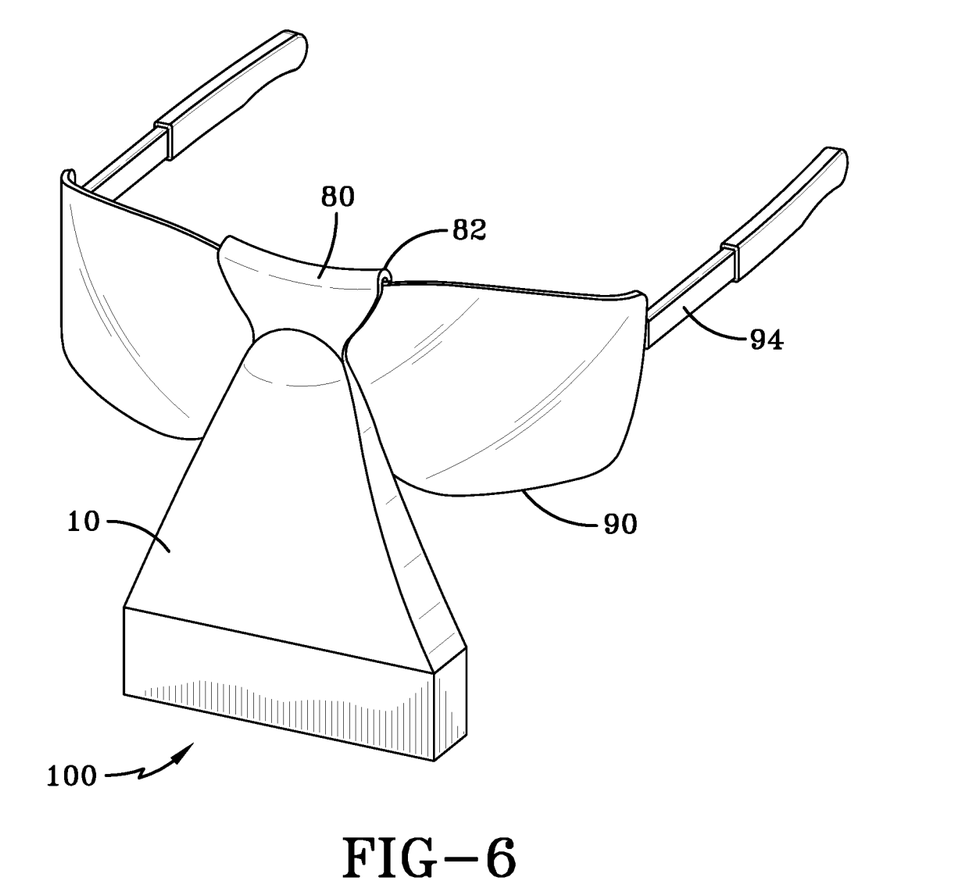
FIG. 6 is a perspective view of the respirator mask of FIG. 5 attached to a pair of glasses.

Referring to FIGS. 5 and 6, in another example, the respirator mask 100 of the present disclosure may be configured to be attached to a pair of glasses 90 (e.g., prescription eyewear, sunglasses, safety glasses/googles, and the like). Such a configuration may enable hands-free use of the of the respirator mask 100. In the example shown, the body 10 may be shaped with an upwards taper such that, when worn by a wearer, the body 10 may extend past the wearer's nose to reach the bridge of a pair of glasses 90. In exemplary embodiments, the body 10 of the respirator mask 100 may also be shaped so as to not obstruct the wearer's vision while being worn. For example, as shown, the body 10 may be inwardly curved along its vertical dimension. Of course, those skilled in the art will appreciate that various other sizes and shapes for the body 10 may also be capable of attachment to a pair of glasses 90. These alternative embodiments may even be capable of attachment to different parts of the glasses 90 (e.g., the temples 94). It is generally contemplated that these differing sizes and shapes may be employed without departing from the scope of the present disclosure.

To facilitate attachment to a pair of glasses 90, the body 10 may include an attachment feature 80. The attachment portion 80 may include any suitable feature, or combinations of features, to effectuate such attachment. In one example, the attachment feature 80 may include a clip 82 that may receive a portion of the bridge in a press fit, friction fit, snap fit, some combination thereof, or the like arrangement (FIG. 6). In another example, the attachment feature 80 may include an adhesive such that the body 10 may be adhered to the bridge of the glasses 90. In yet another example, the respirator mask 100 itself may be fabricated with the glasses 90 as a single monolithic piece.

As those skilled in the art will appreciate, the embodiment of the respirator mask 100 shown in FIGS. 5 and 6 may be provided with any one or more of the components (e.g., filter member 70, interior filter 72, communication device 74, etc.) described above without departing from the scope of the present disclosure.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing device. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

Although various examples of the disclosed face mask 100 have been shown and described, modifications may occur to those skilled in the art upon reading the specification. The present application includes such modifications and is limited only by the scope of the claims.

What is claimed is:
1. A respirator mask comprising:
a body comprising an attachment leature defining a channel for selectively receiving a bridge portion of eyeglasses, said body defining an exterior surface and an interior space;
a mouthpiece comprising an inner channel insertable into a human mouth, wherein the inner channel extends outward from the exterior surface of the body and defines an opening into the interior space;
a nasal interface comprising a recessed portion that is recessed into the body and is configured to receive at least part of a human nose, the nasal interface further comprising a pair of nozzles, wherein each nozzle of the pair of nozzles is insertable into a nostril of a wearer and defines an opening into the interior space;

an additional opening in to the interior space that is configured for intake of external air; and a filtration member within the interior space of the body and fluidly interposed between the additional opening and one or both of the mouthpiece and the nasal interface.

2. The respirator mask of claim 1 wherein:
the body is shaped as a trapezoidal prism comprising a base and a top portion that is wider than the base.

3. The respirator mask of claim 1 wherein:
the mouthpiece further comprises an outer ridge extending from the exterior surface of the body that is configured to surround and enclose at least part of the wearer's mouth.

4. The respirator mask of claim 1 wherein:
a nozzle of said pair of nozzles comprises a proximal portion and a distal portion that is coaxial with said proximal portion, the distal portion being insertable into a nostril of the wearer.

5. The respirator mask of claim 4 wherein:
the proximal portion defines an end surface configured to contact the exterior surface of the wearer's nostril when the wearer inserts the distal portion of the nozzle into the wearer's nostril.

6. The respirator mask of claim 1 wherein:
a nozzle of the pair of nozzles is angled upwards to correspond with the downward orientation of the nasal cavity.

7. The respirator mask of claim 1 further comprising:
a communication device within the interior space of the body that is configured to record and transmit the wearer's voice to an external receiver.

8. A respirator mask comprising:
a body comprising an attachment device for receiving, extending at leat partially about, and frictionally engaging a bridge portion of eyeglasses, said body defining an exterior surface, an interior space, and a first opening into the interior space, wherein the first opening is configured to intake external air;
a mouthpiece comprising an inner channel insertable into a human mouth, wherein the inner channel extends outward from the exterior surface of the body and defines a second opening into the interior space, the mouthpiece further comprising an outer ridge extending from the exterior surface of the body that is configured to surround and enclose at least part of the wearer's mouth; and
a nasal interface comprising a recessed portion that is recessed into the body and is configured to receive at least part of a human nose, the nasal interface further comprising a first nozzle and a second nozzle, wherein the first nozzle and the second nozzle are each insertable into a nostril of a wearer, and wherein the first nozzle defines a third opening into the interior space and the second nozzle defines a fourth opening into the interior space.

9. The respirator mask of claim 8 further comprising:
tubing connected to the first opening that is configured to fluidly couple the respirator mask to a contained air source.

10. The respirator mask of claim 8 wherein:
the inner channel is elongated along the width of the body.

11. The respirator mask of claim 8 wherein:
the recessed portion of the nasal interface comprises an inside surface that defines an edge with the exterior surface of the body, the edge being configured to correspond with the curvature of the human nose.

12. The respirator mask of claim 8 wherein:
the outer ridge of the mouthpiece comprises a crescent shape that defines a pair of longitudinal ends.

13. A respirator mask comprising:
a mask body that defines an exterior surface and an interior space, and which comprises an attachment feature configured to attach the mask body to a pair of glasses, said the attachment feature comprising a clip configured to extend over at least three sides of a bridge portion of eyeglasses and define a channel configured to receive the bridge portion of eyeglasses in a snap fit;
a mouthpiece comprising an inner channel insertable into a human mouth, wherein the inner channel extends outward from the exterior surface of the body and defines an opening into the interior space;
a filter positioned at the interior space, and comprising an air permeable interface for filtering human breath breathed into the mask body and ambient air ingested from outside the mask body; and
a nasal interface comprising a portion that is configured to cover at least part of a human nose, the nasal interface further comprising a pair of nozzles adapted to be inserted into the nostrils of a wearer, said nasal interface defining an opening into the interior space.

14. The respirator mask of claim 13 wherein:
the mask body comprises an upwards narrowing taper so as to not obscure the wearer's vision when the respirator mask is attached to a pair of glasses.

* * * * *